United States Patent [19]

Barr et al.

[11] Patent Number: 4,939,152
[45] Date of Patent: Jul. 3, 1990

[54] CELL CULTURE VIAL

[75] Inventors: Stephen M. Barr, San Jose; Paul A. Rohlf, Mountain View, both of Calif.

[73] Assignee: Syntex (U.S.A.) Inc., Palo Alto, Calif.

[21] Appl. No.: 305,890

[22] Filed: Feb. 2, 1989

Related U.S. Application Data

[62] Division of Ser. No. 102,992, Sep. 30, 1987, Pat. No. 4,845,038.

[51] Int. Cl.$^5$ .............................................. C12M 1/24
[52] U.S. Cl. .................................. 435/296; 435/285; 215/320; 215/354
[58] Field of Search ............... 435/296, 284, 285, 286, 435/287; 215/320, 354, 355

[56] References Cited

U.S. PATENT DOCUMENTS

| | | | |
|---|---|---|---|
| 2,989,204 | 6/1961 | Marx et al. | 141/24 |
| 3,308,039 | 3/1967 | Nelson | 435/295 |
| 4,073,695 | 2/1978 | Lyman | 435/296 |
| 4,140,489 | 2/1979 | Lee | 435/296 |
| 4,308,347 | 12/1981 | Forrer et al. | 435/296 |
| 4,812,408 | 3/1989 | Hammann et al. | 435/296 |

FOREIGN PATENT DOCUMENTS

| | | | |
|---|---|---|---|
| 2443814 | 4/1976 | Fed. Rep. of Germany | 435/296 |
| 2342910 | 3/1976 | France | 215/320 |

Primary Examiner—James C. Yeung
Attorney, Agent, or Firm—Theodore J. Leitereg; Linda J. Nyari; Carole F. Barrett

[57] ABSTRACT

An apparatus for maintaining a biological sample on a support is disclosed. The apparatus comprises a hollow chamber with internal and external surfaces and a first and second end. The first end is open and is adapted for attachment to the first closure means. The second end is either closed or open. If open, the second end is adapted for attachment to a second closure means. The apparatus provides means for maintaining the support in contact with a liquid medium at all times regardless of the orientation of the apparatus. In a preferred embodiment, the apparatus provides means for maintaining the original orientation of a non-integral support regardless of the orientation of the apparatus. The apparatus is useful for isolating and culturing microorganisms.

64 Claims, 6 Drawing Sheets

CELL CULTURE VIAL

BACKGROUND OF THE INVENTION

This is a division of pending application Ser. No. 102,992 filed Sept. 30, 1987, now U.S. Pat. No. 4,845,038, incorporated herein by reference.

1. Field of Invention

This invention relates to an apparatus for maintaining biological samples. The apparatus is particularly suited for transporting or storing adherent material including cell cultures. Additionally, the apparatus is useful for isolating and culturing microorganisms.

Historically, methods for culture confirmation testing, including isolation and identification of a microorganism, require inoculation of cell cultures with patient specimens and incubation to allow growth of the microorganism. Thereafter, the microorganism is detected using a variety of methods including observation of cytopathic effect and microorganism antigen specific confirmation tests. Cell cultures used in such procedures may be adherent, that is, grown attached directly to a support. Such supports include those integral with the container, for example the interior walls of a containing vessel, such as a tube, a microtiter plate, a vial, or the like. Supports also include microscope slides or coverslips, or the like which are not integral with the container.

In those instances where adherent material is stored or transported, it is important to do so without damaging the material. In some cases the support, such as a coverslip, is coated with adherent material and placed in a container which is filled with fluid, for example, cell culture medium. It is important to maintain contact between the adherent material and the fluid to ensure that the material remains viable. It is, therefore, important to maintain a solid fluid column in the containers because during shipment or storage the containers may be tipped or inverted for long periods of time. If a solid column of fluid is not maintained, it is necessary to ensure that containers having biological material on the walls or on a support such as a slide or coverslip are maintained in an upright position.

Additionally, vials used in the past for shipping or storing biological samples lacked a mechanism to ensure that a non-integral support contained therein would retain its original orientation during transportation or storage. If such a support is flipped over so that the adherent material is face down, subsequent procedures, for example an inoculation procedure, are impaired.

A second problem area relates to the handling of a seeded support, that is a support on which biological material is deposited, during procedures such as isolation and culturing biological samples on the seeded material. For example, prior to fixation, some systems require removal of the seeded support from the container in which it has been transported or stored. Such manipulation may involve handling infectious material prior to fixation and, therefore, may result in health hazards. Further, in instances where it is necessary to remove a seeded support from the container to stain the biological material, e.g., the cells, the reagent often flows off of the surface of the support, requiring additional reagent and time to complete the staining procedure. Additionally, if the support is stained after removal from the container, special attention must be given to staining the support evenly. Uneven coverage of the surface of the support causes diminution of staining intensity on poorly covered areas and a "drying edge" artifact on the adherent material. Furthermore, if the support is stained outside of the container, the support is rinsed by immersing it in a waterbath. This procedure requires handling the support with forceps and dipping it into the waterbath. During this procedure, there is a risk that the support will be broken or the adherent material will be damaged.

A support, such as a coverslip, coated with an adherent cell culture is generally removed from a container, such as a tube or vial, by using a bent needle to dislodge the support from the bottom of the container. This task is difficult and is made even more difficult by the presence of fluid beneath the support. After the support is dislodged from the bottom of the container, it is generally removed from the container with a pair of forceps and mounted onto a microscope slide for observation. This process requires skill and considerable dexterity. There is a high risk that the support will be broken or the adherent cell culture will be damaged during the removal procedures.

A cell culturing system called the "Gencell System" has been used for transporting biological samples. The system consists of a cap, a vial and two plastic pieces that are insertable into the vial. One of the insertable plastic pieces is designed to support a coverslip. It is necessary to manually manipulate the coverslip with a forceps to remove it from the insertable pieces. Because the position of the coverslip on the insertable pieces, the coverslip is often removed from the vial prior to staining to economize on reagent. Relatively large volumes of reagent must be used to evenly stain the coverslip if it is not removed from the vial.

There is need, therefore, for an apparatus that will maintain contact between a fluid medium and a support coated with adherent material even if the container is tipped or inverted for long periods of time. In addition, there is need for an apparatus wherein a support being transported in that apparatus will retain its original orientation during shipment. Further, there is need for an apparatus that is adapted for removing a support from it without the use of an instrument, such as a needle or forceps.

2. Description of the Prior Art

U.S. Pat. Nos. 2,665,690; 4,065,358; 4,470,505; 4,342,724 and 3,615,222 disclose multi-compartment containers. Containers and closures are disclosed in U.S. Pat. Nos. 3,432,066; 3,540,612 and 3,592,349. U.S. Pat. Nos. 4,546,085 and 4,321,330 disclose culturing devices. Various closures are disclosed in U.S. Pat. Nos. 3,005,564; 3,164,279; 3,223,269; 3,297,184; 3,370,732; 3,991,895 and 4,094,429.

SUMMARY OF THE INVENTION

The present invention is an apparatus for maintaining a biological sample on a support. The support may be integral with the apparatus itself, for example, an internal side wall or bottom wall of the apparatus. Alternatively, the support may be non-integral, that is it may be separate from and insertable into the apparatus, for example, a microscope slide, a coverslip or the like. The apparatus comprises a hollow chamber, which has internal and external surfaces with a first open end and a second end, which may be open or closed. The apparatus also includes closure means adapted for attachment to the chamber at the first end. As stated, the second end of the chamber may be closed or open. In a preferred embodiment of the present invention, the second end of the chamber is open and the open end is adapted for attachment to a second closure means.

When the apparatus is assembled, the first closure means provides in conjunction with the chamber means for maintaining a solid column of fluid in the apparatus and for maintaining the support in contact with the fluid at all times during transport or storage regardless of the orientation of the apparatus. When the apparatus is assembled such that the first closure means is firmly attached to the first end of the chamber at least two seals are formed between the chamber and the first closure means. At least the outermost seal is liquid tight.

Additionally, in those embodiments wherein the support is not integral with the apparatus, after attachment at the second end of the chamber, the second closure means provides in conjunction with the chamber means for maintaining the original orientation of the support enclosed within the apparatus. Thus, the apparatus of the present invention has the advantage of preventing a non-integral support from turning over during shipping or storage. When the second closure means is firmly attached to the second end of the chamber at least one liquid tight seal is formed between the chamber and the second closure means.

After the apparatus has been filled with fluid and the closure means are firmly attached so as to form liquid tight seals, the apparatus may be inverted and the adherent material on the support will not be exposed to the air. Thus, inversion of the apparatus during shipment or storage will not result in damage to the adherent material, including cells. Additionally, because a solid column of fluid is formed, damage to the adherent material by movement of the fluid in the apparatus is prevented.

The apparatus of the present invention is usable to isolate and culture microorganisms on a support without removing or detaching the support from the apparatus Moreover, in embodiment of the present invention wherein the support is not integrally formed with the apparatus, the support is released and mounted on a surface such as a microscope slide without the use of an instrument, such as a bent needle or forceps.

DESCRIPTION OF THE SPECIFIC EMBODIMENTS

The apparatus of the present invention is useful for maintaining biological material on a support. It is especially useful during shipment and storage of the material. The support may be separately removable from the apparatus such as a coverslip or slide, or may be integral with the apparatus, such as an internal surface of bottom or side wall. The apparatus is also useful for isolating and culturing microorganisms. In its broadest aspect the apparatus comprises a hollow chamber that is open at a first end and has internal and external surfaces. The apparatus also includes a first means adapted for attachment to the first end of the chamber. The chamber also includes a second end. The apparatus also includes a second closure means. The second closure means may be integrally formed with the chamber at its second end, that is, the second end may be closed. Alternatively, the second end may be open and the second closure means may be adapted for attachment to the second open end of the chamber. The first closure means in conjunction with the chamber and second closure means provides means for maintaining the material on the support in contact with a liquid medium at all times, regardless of orientation of the apparatus. The second closure means in conjunction with the chamber provides means for maintaining the original orientation of a non-integral support that is enclosed within the apparatus.

The word support as used herein means any surface on which biological material can be seeded or to which such material adheres. By way of example, but not of limitation, such supports include those that are integrally formed with the apparatus of the present invention, for example, the internal surface of the bottom wall of the second closure means, the internal surface or surfaces of the side wall of the second closure means, the internal surface or surfaces of the chamber or tubular member and the internal surface of the closed end of the chamber or tubular member. The word support as used herein also includes any surface that is not integrally formed with the apparatus of the present invention but is insertable into the second closure means or into the chamber or tubular member. By way of example, but not of limitation, non-integral supports include slides, plates, coverslips, particles, beads and the like. Supports can be made from a variety of materials including, by way of example, metals such as steel; composites, such as ceramics or glass; or plastics, such as nylon, polypropylene, polyethylene, polystyrene, and the like.

In one embodiment of the present invention, the hollow chamber is a tubular member which has internal and external surfaces open at first and second opposed ends.

In another embodiment of the present invention, the hollow chamber is a tubular member with internal and external surfaces open at a first end. A second opposed end is closed. The closed end has an internal and external surface.

The means for maintaining the adherent material on a support in contact with a liquid medium includes means for forming a solid column of fluid in the closed apparatus, which include sealing means located between the chamber or tubular member and the first closure means. Such sealing means includes first stopping means on the internal surface of the tubular member. The first stopping means is preferably proximate the first end of the chamber. When the first closure means is firmly attached to the chamber or tubular member, contact is made between the first closure means and the first stopping means. The first stopping means is preferably an annular ledge. In one preferred embodiment, the annular ledge is beveled and contacts a beveled surface on the first closure means when the first closure means is firmly attached to the first end of the tubular member. The angle of the beveled surface on the first closure means is generally approximately 10°-60°, preferably 35°-50° off horizontal and the angle of the beveled annular ledge on the tubular member is generally approximately 5° to 45°, preferably 25°-40° off horizontal.

The means for maintaining contact between the biological material and the fluid also includes formation of a second sealing means between the chamber or tubular member and the first closure means. By way of example, but not limitation, such liquid sealing means includes the internal surface of the chamber or tubular member, a surface of the first closure means, and at least one annular ring on the internal surface of the chamber or tubular member between the first stopping means and its first end. Such liquid sealing means may also include at least one annular ring on the exterior surface of the chamber or tubular means. The second sealing means is preferably proximate the first end of the tubular member or chamber. In another embodiment of the present invention, the second sealing means is at least one annular ring on the internal surface of the second annular skirt of the first closure means. Such a means is preferably close to the top portion of the first closure means.

The means for maintaining contact between the biological material and the fluid also optionally includes a third sealing means between the chamber or tubular member and the first closure means. By way of example, but not of limitation, such sealing means includes at least one annular ring on the external surface of the first annular skirt of the first closure means, at least one annular ring on the internal surface of the second annular shirt of the first closure means, at least one annular ring on the internal or external surface of the chamber or tubular member.

The apparatus of the present invention allows a solid column of fluid to be formed such that the sample being maintained therein is in constant contact with the fluid no matter what orientation is given the apparatus. This is accomplished by filling the apparatus containing the adherent biological sample with fluid so that the fluid is slightly above the first stopping means. The fluid above the first stopping means is "excess" fluid. When first closure means is inserted into the first end of the tubular member and is firmly attached to the tubular member, the first stopping means contacts the first closure means to create a first sealing means. In a preferred embodiment the first sealing means will comprise the junction of two beveled surfaces. The first closure means also contacts the tubular member to form a second sealing means preferably located between the first sealing means and the first end of the tubular member and forms a seal. The excess fluid is forced past the first sealing means and into a space defined between the first closure means and the the tubular member by the first and second sealing means. Because the excess fluid is trapped in the space it will not contaminate the sample or the user.

The tubular member optionally includes a grasping means on its external surface. The grasping means is generally located near the second end of the tubular member. By way of example, the grasping means includes at least one rib, ridge, projection or groove, an embossed or textured surface or the like.

The first closure means may comprise a plug that firmly contacts the first stopping means when the first closure means is firmly attached to the first end of the tubular member. The plug may be solid or hollow. In a preferred embodiment of the present invention, the plug comprises a hollow cylinder having an open end and a closed end formed by a bottom wall having internal and external surfaces. The plug has a downwardly depending skirt or side wall that is adapted to fit into the first open end of the tubular member. In a preferred embodiment, the plug includes a beveled surface at the junction of the bottom wall and the skirt.

In a preferred embodiment, the first closure means includes a second downwardly depending annular skirt or wall. The second skirt has internal and external surfaces and is attached to and depends from a top portion of the first closure means, generally from the periphery of the top portion. The internal diameter of the second skirt is greater than the external diameter of the first end of the tubular member.

The second skirt may be the same length as the first skirt or it may be shorter than or longer than the first skirt. In a preferred embodiment of the first closure means, the second or outer skirt is longer than the first, inner skirt. Such a configuration allows handling of the apparatus to remove the first closure means from the first end of the tubular member without contacting any fluid that adheres to the first closure means.

Additionally, the first closure means optionally includes means for gripping or grasping it to aid in the removal of the closure means from the tubular member. By way of example, but not of limitation, such gripping means include raising the external surface of the second annular skirt such as by embossment or texturing, or by projections such as ribs or ridges. Likewise, gripping means includes indenting the external surface of the second annular skirt, for example, by placement of grooves in the surface. Additionally, the gripping means includes a septum which is preferably flat and vertical and is mounted on or attached to opposed sides of the hollow cylinder or plug. The external surface of the septum may be smooth or textured for example with ribs or embossments to facilitate gripping. The septum may also have at least one hole in or through its surface to allow insertion of an instrument for grasping the first closure means or for removing the first closure means from the tubular member.

The first closure means has two closure positions. For example, certain types of biological material require an increased partial pressure of atmospheric carbon dioxide to promote optimal growth. In these cases the first closure means is placed loosely on the tubular member, allowing gas exchange to take place. In those instances where it is important to ensure that a liquid tight seal is formed, e.g. during transportation of the apparatus of the present invention, or where biological or other material not requiring carbon dioxide is utilized, the first closure means is firmly attached to the tubular member so as to be in the full closure position.

In those embodiments of the present invention wherein the second end of the chamber is closed, the second closed end is the second closure means. In those embodiments of the present invention wherein the second end of the chamber is open, the second closure means preferably includes an open end, a side wall with internal and external surfaces and a closed end formed by a bottom wall with internal and external surfaces. In one embodiment, the second closure means is cylindrical.

The means for maintaining the original orientation of a non-integral support which is insertable into the second closure means includes means for maintaining a certain distance between the second open end of the tubular member and the internal surface of the bottom wall of the second closure means when the tubular member and the second closure means are firmly attached. This distance is less than the internal diameter of the second closure means, less than the diameter of a non-integral support and less than the internal diameter of the second open end of the tubular member. The internal diameter of the second open end of the tubular member is also less than the diameter of the non-integral support. Such means include, by way of example, but not of limitation, a second stopping means located on the external surface of the tubular member proximate its second end, including at least two discontinuous projections, an annular ring, an annular shoulder or the like. In another preferred embodiment, the second stopping means is located on the internal surface of the second closure means. Such means include narrowing the internal diameter of the second closure such that the second end of the chamber contacts a narrowed portion of the internal surface of the second closure means, an annular shoulder, discontinuous projections or the like.

A second stopping means is optionally located on the second closure means. In a preferred embodiment, the internal surface of the side wall of the second closure means protrudes or is narrowed or indented such that when the second closure means is firmly attached to the chamber or tubular member, the side wall provides a stopping means for maintaining the distance between the second open end of the chamber or tubular member and the internal surface of the bottom wall. In this embodiment, the second end of the tubular member contacts the indented or protruding portion of the internal surface of the side wall.

In the apparatus of the present invention, a liquid tight seal is formed between the chamber or tubular member and the second closure means. In embodiments wherein the second closure means is detachable from the chamber, such sealing means includes by way of example, but not of limitation, at least one annular ring, ridge, projection or shoulder on the external surface of the chamber or tubular member near its second end or at least one annular ring, ridge, projection or shoulder on the internal surface of the side wall of the second closure means. Alternatively, the second closure means and the tubular member may form a liquid tight seal by friction or interference.

The external surface of the second closure means optionally includes a grasping means. Such means include by way of example, but not of limitation, embossment, texturing, annular rings, projections, ridges, ribs or grooves.

The second closure means of the present invention optionally includes means for releasing a non-integral support from the internal surface of its bottom wall. By releasing means is meant any means or combination of means used alone or in combination with pressure to reduce adherence of a non-integral support to the internal surface of the bottom wall of the second closure means including means for withdrawing fluid from beneath the support. The releasing means includes by way of example, but not by way of limitation, embossment or texturing on the internal surface of the bottom wall, at least one groove on the internal surface of the bottom wall, at least one projection, such as a post or a ridge on the internal surface of the bottom wall or at least one longitudinal groove on the internal surface of the side wall of the second closure means. In another embodiment, the releasing means includes a fexible bottom wall on the second closure means. Such means allow the support to be easily removed from the internal surface of the bottom wall by exerting pressure, for example with a finger, pipette tip, pencil eraser, or the like, on the external surface of the bottom wall. In another embodiment, the releasing means includes a beveled surface or a shoulder at the junction of the internal surface of the side wall and internal surface of the bottom wall. Preferably, the height of the second closure means is less than the diameter of the non-integral support, so that when the second closure means is inverted the support falls so that the adherent material is face down on an object on which it falls, such as a microscope slide.

The apparatus of the present invention may be adapted for the detection of a biological sample without removal of the sample from the apparatus in embodiments wherein either or both of the bottom walls of the first and second closure means are composed of translucent or transparent material. Thus, the first and/or second closure means provide optical clarity along the vertical axis of the apparatus. For example, in an embodiment wherein the bottom walls of the first and second closure means are composed of transparent or translucent material, the sample is observable with both standard and inverted orientation light microscopes without damaging the adherent material. Other instruments, e.g. spectrophotometers may be employed to analyze the sample.

The apparatus of the present invention may be made from a variety of materials or combinations of materials including, by way of example, but not of limitation, metal such as steel, ceramics, glass, and plastics, such as nylon, polypropylene, polyethylene, polystyrene, and the like. In those embodiments wherein a non-integrally formed support, such as a coverslip or slide, is used hydrophobic plastics, such as polypropylene may be preferred. Polypropylene offers additional advantages because it can be optically clear, biologically inert and resistant to acetone, which is often used as a fixative.

Cells that are adherent to the support may be fixed without being removed from the apparatus of the present invention. This eliminates any unnecessary manipulation and avoids the possible health hazard of handling infectious material prior to fixation. If a fixative will be used, it is important to select an apparatus constructed of a material that is compatible with the fixative. For example, polypropylene and glass have been found to be compatible with acetone fixation.

In a preferred embodiment, cells can be stained without being removed from the apparatus of the present invention. To reduce the volume of reagent necessary for staining, the apparatus may be constructed of a hydrophobic material, thus allowing a support to be stained in the apparatus using only about 40-100 μL, preferably 50-75 μL of reagent. Therefore, in addition to reducing manipulation of the material, use of the apparatus for staining provides economy of reagent.

The biological material may be rinsed without removing it from the apparatus, thus avoiding breaking an insertable support or damaging the biological material during removal from the apparatus or immersion in a waterbath. The material is rinsed by adding the rinsing solution such as phosphate buffered saline (PBS), deionized or distilled water, or the like, to the apparatus or to the second closure means and swishing gently.

The apparatus in accordance with the present invention can be further illustrated by reference to the attached drawings.

FIGS. 1, 1A, 2 and 2A are illustrative of one embodiment of the present invention. Now referring to FIGS. 1, 1A and 2, hollow chamber 10 is preferably a tubular member with internal 11 and external 12 surfaces, which are open at first 13 and second 14 ends. The apparatus also includes first closure means 15 and second closure means 16, which are adapted for attachment to chamber 10 at its first 13 and second 14 open ends, respectively.

The particular volume of the device of the present invention will depend upon the intended use of the device and the biological material being transported, stored or analyzed. Preferably the device has an external diameter that will be accepted by low volume centrifuge buckets used in many laboratories. Normally, a capacity of 2 mL to 25 mL is considered to be a practical range when the device is fully assembled. Often the capacity is 2 mL to 15 mL, and more usually 2 mL to 10 mL.

Figure 1:
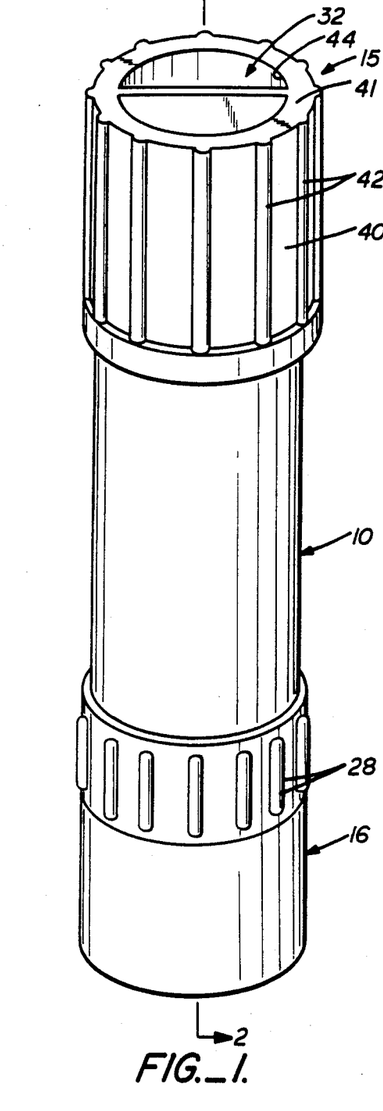
FIG. 1 is an isometric view of a device in accordance with one embodiment of the present invention.
Figure 1A:
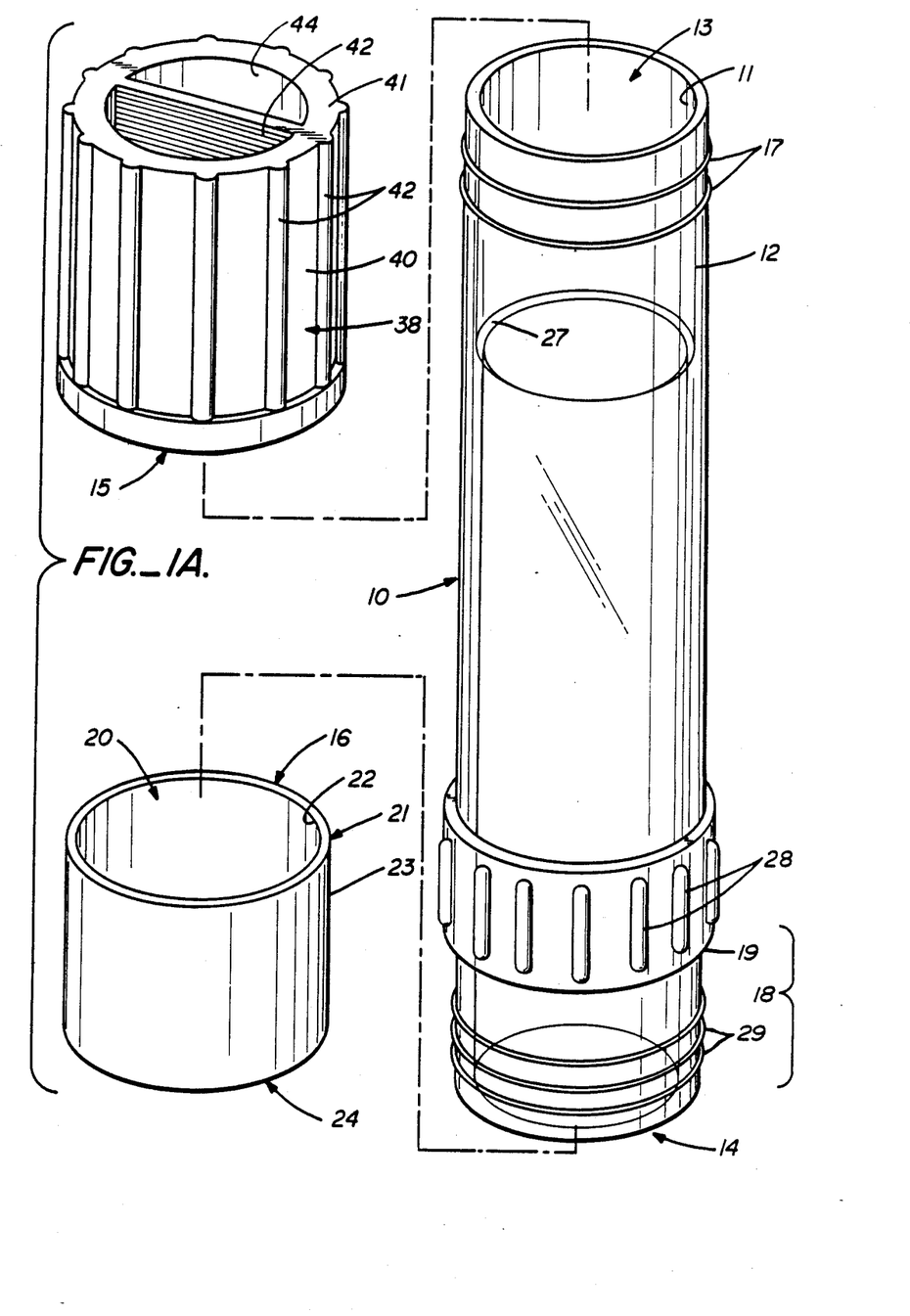
FIG. 1A is an exploded isometric view of the first closure means, the second closure means and the chamber in accordance with FIG. 1.
Figure 2:
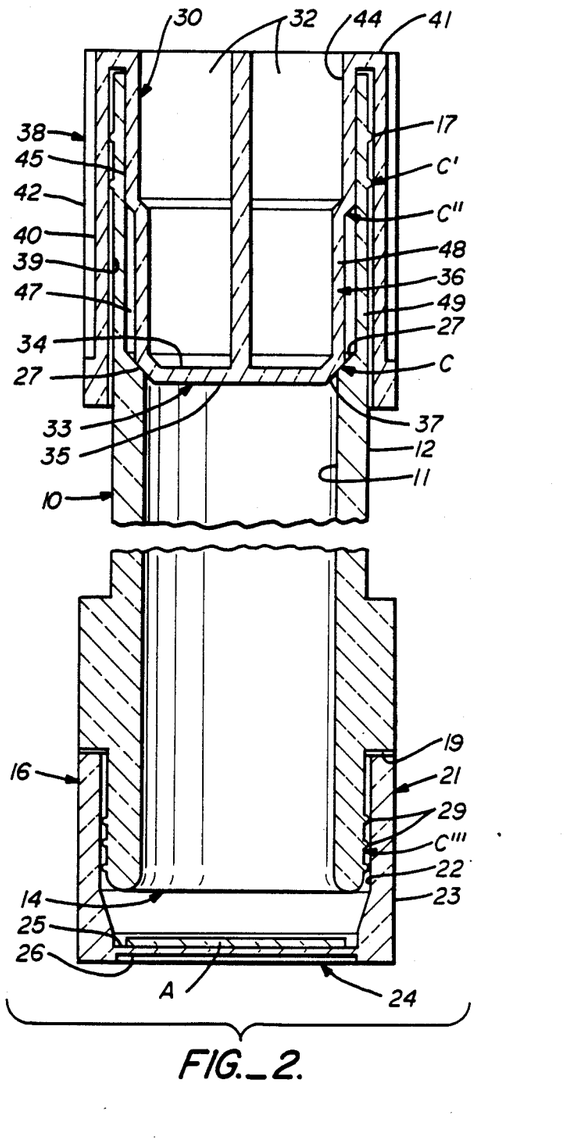
FIG. 2 is a side elevation view in cross-section of the device taken along lines 2—2 of FIG. 1.

After the apparatus of the present invention is assembled, first closure means 15 provides in conjunction with chamber 10 means for maintaining contact between biological material adherent to a support and a liquid medium in the apparatus regardless of the orientation of the apparatus. Such means include means for forming a solid column of liquid in the apparatus including at least two sealing means, C and C'. First sealing means C includes first stopping means 27 on internal surface 11 of chamber 10 in conjunction with bevelled surface 37 of first closure means 15. First stopping means 27 may be an annular ledge. First stopping mean 27 may be beveled.

Means for maintaining a solid column of fluid also includes second sealing means C' for forming a liquid tight seal between chamber 10 and first closure means 15. As shown, second sealing means C' includes by way of example, but not of limitation, at least one annular ring 17 on external surface 12 of chamber 10 located close to its first end 13 in conjunction with internal surface 39 of second annular skirt 38. As shown, the apparatus also includes optional sealing means C'', which by way of example is located at the junction of the internal surface 11 of chamber 10 and first closure means 15 between first sealing means C and second healing means C'.

First closure means 15 includes plug 30 adapted to firmly contact first stopping means 27 when first closure means 15 is firmly attached to chamber 10. As shown, plug 30 is hollow and has open 32 and closed 33 ends and downwardly depending first internal annular skirt 36 with internal (44) and external (45) surfaces adapted to fit into first open end 13 of chamber 10. Annular skirt 36 has internal and external surfaces, respectively.

Closed end 33 is formed by a bottom wall with internal 34 and external 35 surfaces. Plug 30, as illustrated, may include beveled surface 37 adapted to contact first stopping means 27 which, as indicated above, may be beveled. The angle of beveled surface 37 of first closure means 15 is generally about 10°-60°, preferably about 35°-50° off horizontal and the angle of the beveled annular ledge is generally about 5°-45°, preferably about 25°-40° off horizontal.

First closure means 15 includes second annular skirt 38 having internal 39 and external 40 surfaces. Second annular skirt 38 is generally attached to and depending from a top portion 41 of first closure means 15. The diameter of second annular skirt 38 is greater than the external diameter of first open end 13 of chamber 10. First (internal) 36 and second (external) 38 annular skirts optionally are the same length or different lengths. In a preferred embodiment as is shown, second annular skirt 38 is longer than the first annular skirt 36.

Figure 3:
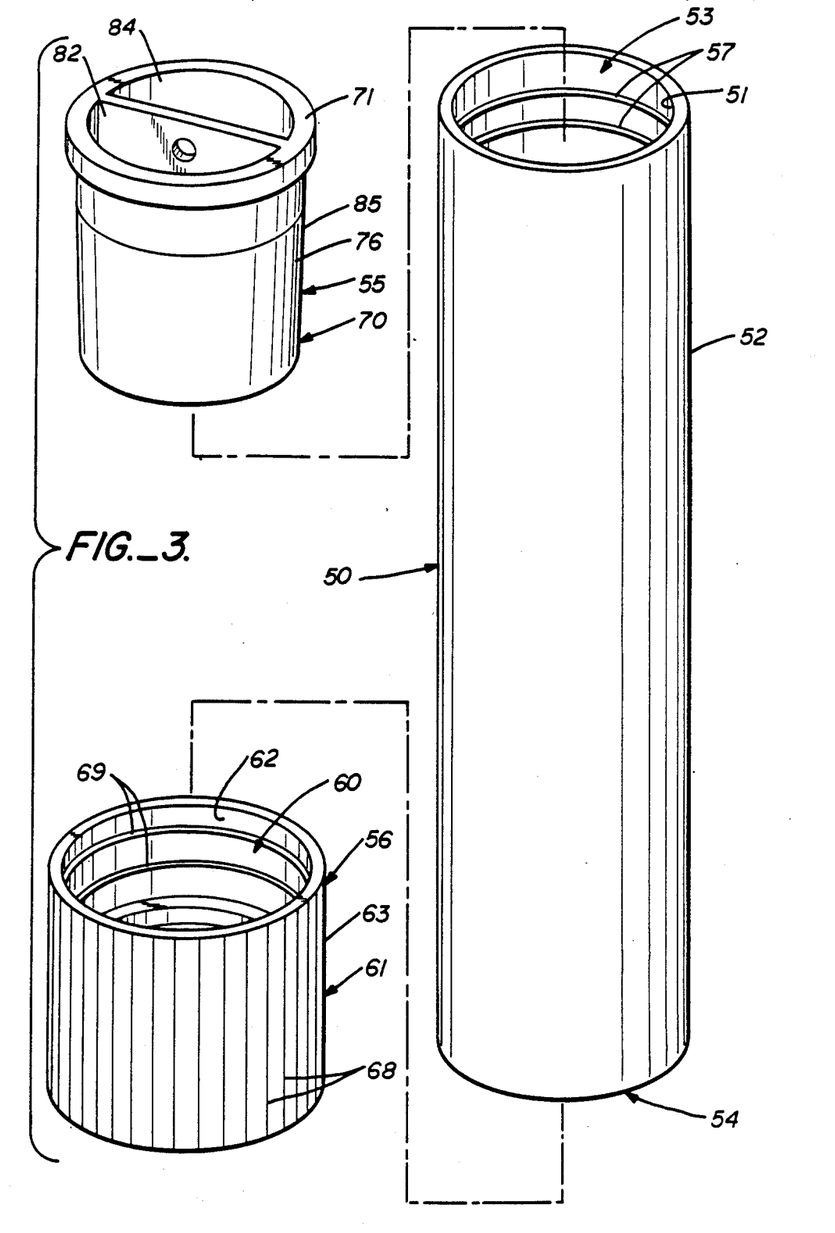
FIG. 3 is an exploded isometric view of another embodiment of a first closure means, a second closure means and a chamber in accordance with the present invention.

First closure means 15 includes gripping means 42. Such gripping means 42 are optionally located on external surface 40 of second annular skirt 38 and includes by way of example, grooves, embossments or at least one ridge or rib as illustrated in FIG. 1A. Such gripping means 42 are optionally mounted within the first closure means 15 so as to be attached to or integrally formed with internal surface 44 of first annular skirt 36. Such means include by way of example, but not of limitation, a septum attached to opposite sides of plug 30. The surface of the septum is optionally smooth or textured and may include grooves. The septum may also have one or more holes in its surface as shown in FIG. 3 to allow insertion of an instrument, such as a needle or forceps.

To produce a solid column of fluid within the appartus, the apparatus is filled with fluid so that the fluid level is slightly above first stopping means 27. The amount of fluid above the first stopping means is equal to or less than the amount of fluid that will fit in space 47. First closure means 15 is inserted into first open end 13 of tubular member 10 so that surface 37 contacts first stopping means 27 and form sealing means C. The liquid that was above the first stopping means 27 is forced into space 47 bounded by first sealing means C, lower portion 48 of external surface 45 of internal skirt 36, portion 49 of internal surface 11 of tubular member 10 and optional sealing means C''. The excess liquid remains in space 47 during transport or storage of the apparatus.

As mentioned above, the apparatus of the present invention includes second sealing means C' for forming a liquid tight seal between chamber 10 and first closure means 15. Such means, as indicated above, include at least one annular ring 17 located on external surface 12 of chamber 10 close to its first end 13. The annular ring or rings are located such that when first closure means 15 is firmly attached to the chamber 10, the annular ring or rings contact internal surface 39 of second annular skirt 38.

The apparatus of the present invention includes means 18 for maintaining the original orientation of a non-integral support. Continuing to refer to FIGS. 1, 1A and 2, in a preferred embodiment such means 18 may include second stopping means 19 on external surface 12 of chamber 10 near its second end 14 in conjunction with a surface of second closure means 16. Second stopping means 19, as illustrated, includes an annular shoulder on external surface 12 of chamber 10.

Second closure means 16 has open end 20, is closed by bottom wall 24 having internal 25 and external 26 surfaces and has side wall 21 with internal surface 22 and external surface 23. The dimensions of the device of the present invention vary, however, when chamber 10 is firmly attached to second closure means 16, the distance between second open end 14 of chamber 10 and internal surface 25 of bottom wall 24 is less than the internal diameter of second open end 14 of chamber 10, and less than the diameter of support A, and the internal diameter of second open end 14 of chamber 10 is less than the diameter of support A. For example, in those instances where the adherent material is seeded on a support having a diameter of 12 mm, the internal diameter of the second closure means will be greater than 12 mm and the internal diameter of the tubular member at its second end will be less than 12 mm.

Figures 2A, 4, 5:
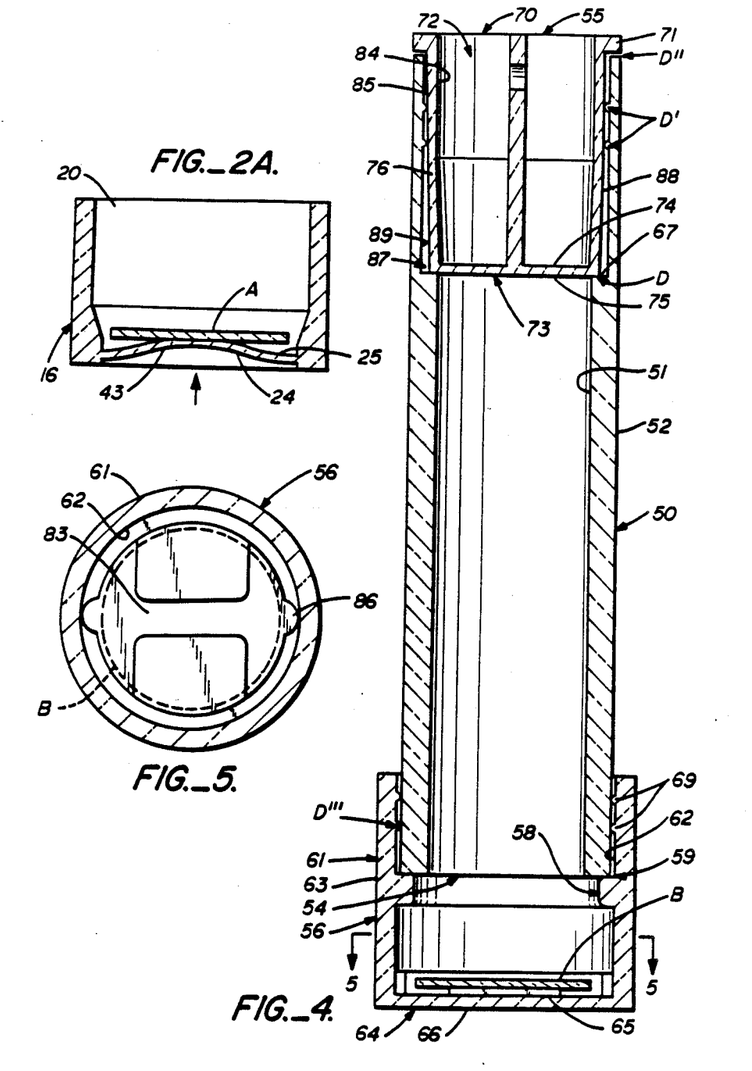
FIG. 2A is a side elevation view in cross-section of a second closure means in accordance with one embodiment of the present invention
FIG. 4 is a side elevation view in cross section of the assembled first and second closure means and chamber of FIG. 3.
FIG. 5 is a top plan view in cross-section of the second closure means taken along lines 5—5 of FIG. 4.

The junction of internal surface 22 of side wall 21 of second closure means 16 and internal surface 25 of bottom wall 24 is optionally beveled or form a shoulder as illustrated in FIGS. 2 and 2A.

It should be understood as within the present invention that the apparatus may be adapted so that the biological material is seeded on the internal surface 25 of bottom wall 24 of second closure means 16. In such an embodiment internal surface 25 of bottom wall 24 of second closure means 16 is adapted for use as a support.

The apparatus of the present invention optionally includes grasping means 28 in addition to or in place of gripping means 42. Such grasping means 28 may be located either on external surface 12 of chamber 10 or on external surface 23 of side wall 21 of second closure means 16 or on both surfaces. By way of example, but not of limitation, such grasping means 28 includes ribs, ridges as shown in FIGS. 1 and 1A, grooves, or embossment or texturing as shown in FIG. 3.

Continuing to refer to FIGS. 1, 1A, 2 and 2A, the apparatus of the present invention includes sealing means C''' for forming a liquid tight seal between second closure means 16 and chamber 10. By way of example, but not of limitation, such sealing means C''' includes at least one annular ring 29 on external surface 12 of chamber 10 near its second end 14, in conjunction with internal surface 22 of second closure means 16.

Figure 7:
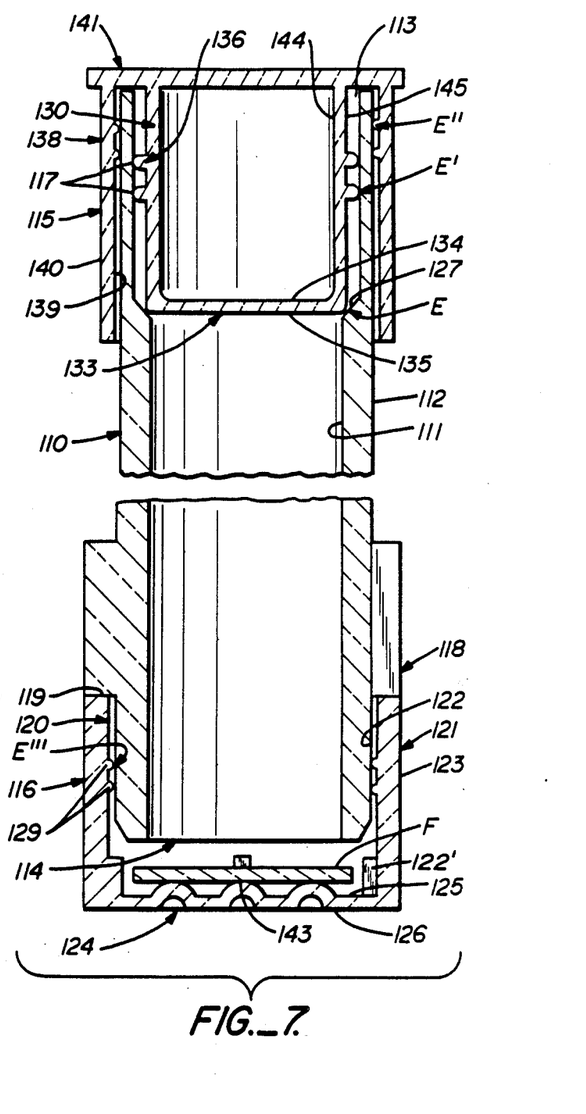
FIG. 7 is a side elevation view in cross section of the device taken along lines 7—7 of FIG. 6.

The apparatus of the present invention optionally includes releasing means 43 for releasing a support from internal surface 25 of bottom wall 24 of second closure means 16. By way of example, but not of limitation, the releasing means includes at least one groove 83 on internal surface 65 of bottom wall 64 of second closure means 56, as illustrated in FIGS. 4 and 5; at least one protuberance on internal surfaces 25 and 125 of bottom walls 24 and 124 of second closure means 16 and 116, as illustrated in FIGS. 2A and 7, respectively; and at least one groove 86 in internal surface 62 of side wall 61 of second closure means 56, as illustrated in FIG. 5. Such releasing means 43 also includes a flexible bottom wall 24 on second closure means 16 such that the bottom wall 24 may be distended to release the support.

FIGS. 3-5 are illustrative of another embodiment of the present invention. The numbering convention used in FIGS. 3-5 have been designed so that the second digit of the number is the same as the second digit of the number of the corresponding element in the apparatus depicted in FIGS. 1, 1A and 2. Tubular member 50 with internal 51 and external 52 surfaces, which are open at first 53 and second 54 ends. The apparatus also includes first closure means 55 and second closure means 56, which are adapted for attachment to tubular member 50 at its first 53 and second 54 open ends.

After the apparatus of the present invention is assembled, first closure means 55 provides in conjunction with tubular member 50 means for maintaining contact between biological material on support B and a liquid medium in the apparatus regardless of the orientation of the apparatus. Support B may be insertable as shown or in the alternative may be one or more internal surfaces of second closure means 56, that is internal surface 62 or 65 of side wall 61 or bottom wall 64, respectively, of second closure 56.

Continuing to refer to FIGS. 3-5, tubular member 50 includes first stopping means 67 on its internal surface 51. First stopping means 67 is an annular ledge. First closure means 55 includes plug 70 with internal (84) and external (85) surfaces, adapted to firmly contact first stopping means 67 when first closure means 55 is firmly attached to tubular member 50. As shown, plug 70 is hollow and has open 72 and closed 73 ends and downwardly depending skirt 76 adapted to fit into first open end 53 of tubular member 50. Closed end 73 is formed by a bottom wall with internal 74 and external 75 surfaces. Plug 70, as illustrated, is adapted so that external surface 75 of bottom wall 73 contacts first stopping means 67 to form first sealing means D. Second sealing means D' for forming a liquid tight seal between tubular member 50 and first closure means 55 includes at least one annular ring 57 on internal surface 51 of tubular member 50 located close to its first end 53 in conjunction with external surface 85 of plug 70. Thus, annular ring or rings are located such that when first closure means 55 is firmly attached to tubular member 50, the annular ring or rings contact external surface 85 of plug 70.

After insertion of second end 54 of tubular member 50 into open end 60 of second closure means 56, fluid is poured into the apparatus of the present invention such that the top of the fluid level is slightly above first stopping means 67. Thereafter, plug 70 is inserted into first open end 53 of tubular member 50. Exterior surface 75 of bottom wall 73 of plug 70 firmly contacts first stopping means 67 to form sealing means D. The fluid which was originally above first stopping means 67 is forced into space 87 bound by sealing means D, lower portion 88 of external surface 85 of plug 70 and portion 89 of internal surface 51 of tubular member 50 and sealing means D'.

First closure means 55 also includes a top portion 71 that contacts first open end 53 of tubular member 50 when the first closure means 55 is firmly attached to the tubular member 50 forming optional sealing means D''.

First closure means 55 includes gripping means 82, which may be mounted within first closure means 55 so as to be attached to or integrally formed with internal surface 84 of plug 70. Such means includes by way of example, but not of limitation, a septum attached to opposite sides of plug 70 and may include grooves or one or more holes in its surface as shown in FIG. 3 to allow insertion of an instrument, such as a needle or forceps.

Second closure means 56 has open end 60, is closed by bottom wall 64 having internal 65 and external 66 surfaces and has side wall 61 with internal surface 62 and external surface 63.

The apparatus of the present invention includes means 58 for maintaining the original orientation of an non-integral support B. Use of a non-integral support, as has been mentioned, is optional. The biological material may be adhered directly on one or more surfaces of tubular member 50 or second closure means 56. Continuing to refer to FIGS. 3-5, in a preferred embodiment such mean 58 includes stopping means on internal surface 62 of side wall 61 of second closure means 56. The stopping means, as illustrated, includes an annular shoulder or a narrowing of the internal diameter of side wall 61 such that when tubular member 50 is firmly attached to second closure means 56 second end 54 of tubular member 50 contacts the annular shoulder or narrowed portion of side wall 61 forming stopping means 59. In those embodiments wherein support B is separately insertable, the distance between second open end 54 of tubular member 50 and internal surface 65 of bottom wall 64 is less than the internal diameter of second open end 54 of tubular member 50, and less than the diameter of support B, and the internal diameter of second open end 54 of tubular member 50 is less than the diameter of support B.

Continuing to refer to FIGS. 3-5, the apparatus of the present invention includes sealing means D''' for forming a liquid tight seal between second closure means 56 and tubular member 50. By way of example, but not of limitation, sealing means D''' includes at least one annular ring 69 on internal surface 62 of side wall 61 of second closure means 56 in conjunction with external surface 52 of tubular member 50.

The apparatus of the present invention also includes grasping means 68 in addition to or in place of gripping means 82. Such grasping means 68 may be located on external surface 63 of side wall 61 of second closure means 56. By way of example, but not of limitation, grasping means 68 includes embossment or texturing as shown in FIG. 3.

As discussed above, the apparatus of the present invention optionally includes releasing means 83 for releasing non-integral support B from internal surface 65 of bottom wall 64 of second closure means 56. As illustrated in FIGS. 4 and 5, releasing means 83 includes at least one groove on internal surface 65 of bottom wall 64 of second closure means 56 or at least one groove in internal surface 62 of side wall 61 of second closure means 56.

Figure 6:
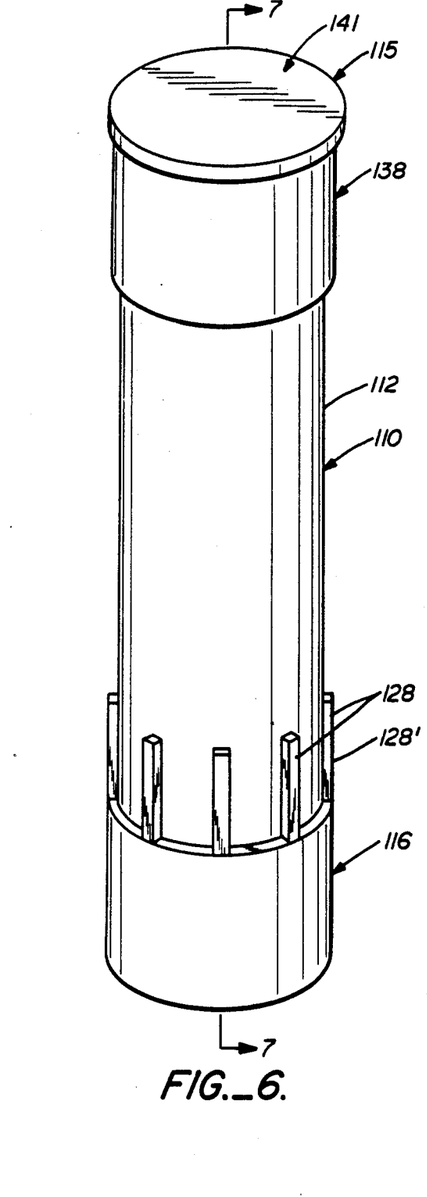
FIG. 6 is an isometric view of another embodiment of a device in accordance with the present invention.

FIGS. 6 and 7 are illustrative of another embodiment of the present invention. The numbering convention used in FIGS. 6 and 7 has been designed so that the last two digits of the number is the same as the two digit number of the corresponding element in the apparatus depicted in FIGS. 1, 1A and 2. Now referring to FIGS. 6 and 7, tubular member 110 has internal 111 and external 112 surfaces, which are open at first 113 and second 114 ends. The apparatus also includes first closure means 115 and second closure means 116, which are adapted for attachment to tubular member 110 at its first, 113 and second, 114 open ends, respectively.

Tubular member 110 includes first stopping means 127 on internal surface 111 of tubular member 110. First stopping means 127 may be an annular ledge which is beveled. First closure means 115 includes plug 130 adapted to firmly contact first stopping means 127 to form first sealing means E when first closure means 115 is firmly attached to tubular member 110. As shown, plug 130 has closed end 133, and closed top portion 141. Internal skirt 136 having internal and external surfaces 144 and 145, respectively depends from top portion 141 and is adapted to fit into first open end 113 of tubular member 110. Closed end 133 is formed by a bottom wall with internal 134 and external 135 surfaces. Plug 130, as illustrated, is adapted to contact first stopping means 127 which, as indicated above, is an optional beveled annular ledge forming first sealing means E.

First closure means 115 includes second annular skirt 138 having internal 139 and external 140 surfaces. Second annular skirt 138 is generally attached to and depends from top portion 141. The diameter of second annular skirt 138 is greater than the external diameter of first open end 113 of tubular member 110.

After the apparatus of the present invention is assembled, first closure means 115 provides in conjunction with the tubular member 110 means for maintaining contact between a support and a liquid medium in the apparatus regardless of the orientation of the apparatus. Such means includes first sealing means E, as discussed above and second sealing means E' for forming a liquid tight seal between tubular member 110 and first closure means 115. As shown in the present embodiment by way of example, but not of limitation, sealing means E' includes at least one annular ring 117 on external surface 145 of first annular skirt 136 of first closure means 115 in conjunction with internal surface 111 of tubular member 110. The annular ring or rings are located such that when first closure means 115 is firmly attached to tubular member 110, second sealing means E' is formed.

As shown, the apparatus also includes optional sealing means E'', which by way of example is located at the junction of external surface 112 of tubular member 110 and internal surface 139 of second annular skirt 138 of first closure means 115. Optional sealing means 3'' may include at least one annular ring on external surface 112 or on internal surface 139.

The apparatus of the present invention includes means 118 for maintaining the original orientation of support F. Continuing to refer to FIGS. 6 and 7, in a preferred embodiment such means 118 includes second stopping means 119 on external surface 112 of tubular member 110 near its second end 114 in conjunction with a surface of second closure means 116. Second stopping means 119, as illustrated, includes at least two discontinuous projections 128' on external surface 112 of tubular member 110. The apparatus of the present invention also include grasping means 128.

Second closure means 116 has open end 120, is closed by bottom wall 124 having internal 125 and external 126 surfaces and has side wall 121 with internal surface 122 and external surface 123. When tubular member 110 is firmly attached to second closure means 116, the distance between second open end 114 of tubular member 110 and internal surface 125 of bottom wall 124 is less than the internal diameter of second open end 114 of tubular member 110, and less than the diameter of support F, and the internal diameter of second open end 114 of chamber 110 is less than the diameter of support F. The junction of internal surface 122 of side wall 121 of second closure means 116 and internal surface 125 of bottom wall 124 optionally form a shoulder 122' as illustrated in FIG. 7.

Continuing to refer to FIGS. 6 and 7, the apparatus of the present invention includes sealing means E''' for forming a liquid tight seal between second closure means 116 and tubular member 110. By way of example, but not of limitation, such sealing means E''' includes at least one annular ring 129 on internal surface 122 of side wall 121 of second closure means 116.

The apparatus of the present invention optionally includes releasing means 143 for releasing support F from internal surface 125 of bottom wall 124 of second closure means 116. By way of example, but not of limitation, releasing means 143 includes at least one protuberance or projection on internal surface 125 of bottom wall 124 of second closure means 116, as illustrated in FIG. 7.

Figures 8, 9:
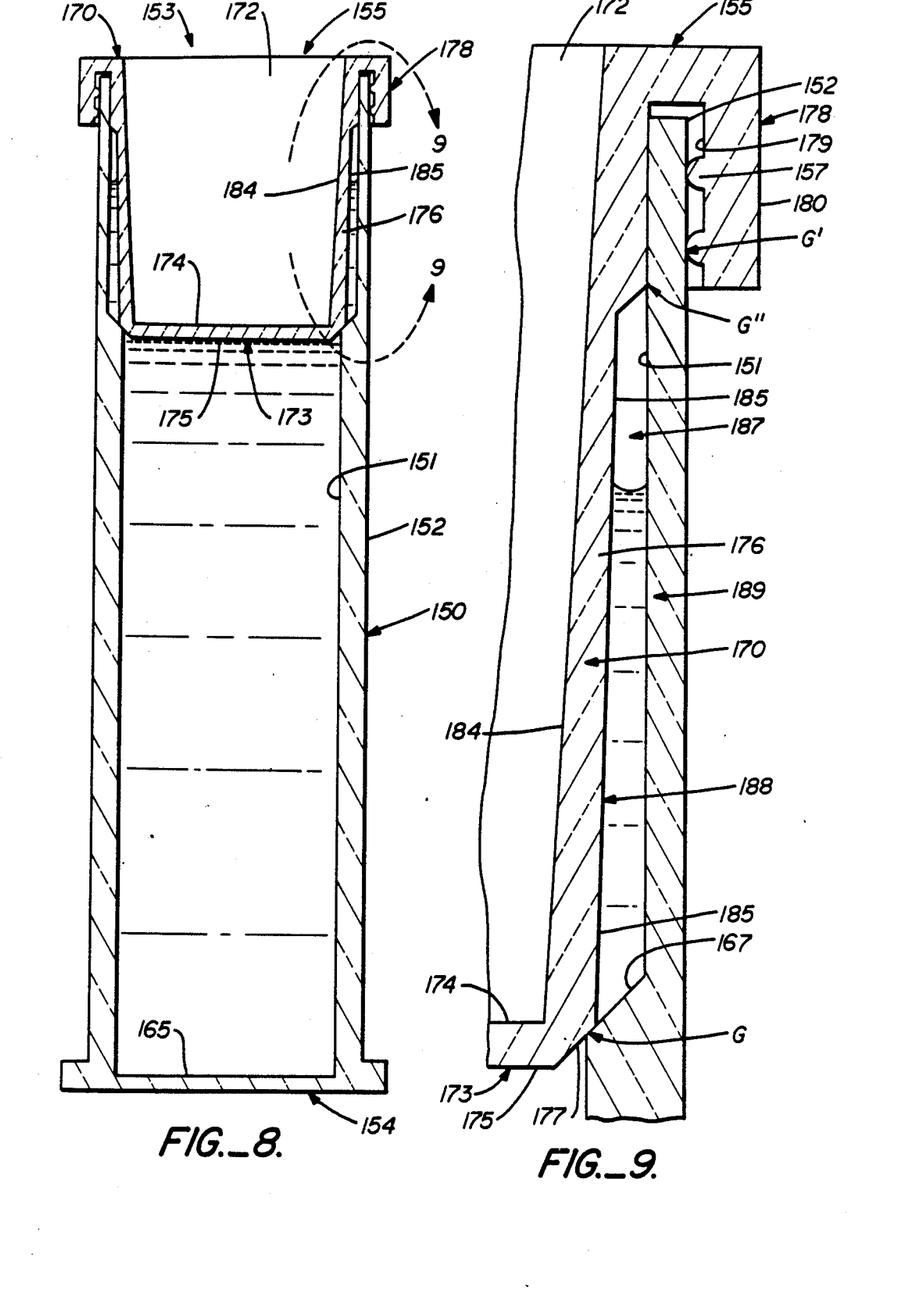
FIG. 8 is a side elevation view in cross section of a device in accordance with one embodiment of the present invention.
FIG. 9 is an enlarged view of a portion of FIG. 8 indicated along dashed line 9—9.

FIGS. 8 and 9 are illustrative of another embodiment of the present invention. The numbering convention used in FIGS. 8 and 9 has been designed so that the second two digits of the number is the same as the second two digits of the number of the corresponding element in the apparatus depicted in FIGS. 3-5. Tubular member 150 with internal 151 and external 152 surfaces, which are open at first end 153 and closed at second end 154. The apparatus also includes first closure means 155 which is adapted for attachment to tubular member 150 at its first open end 153.

After being attached firmly to tubular member 150, first closure means 155 provides in conjunction with tubular member 150 means for maintaining contact between biological material on internal surface 165 of second end 154 and/or on internal surface 151 of tubular member 150, and a liquid medium in the apparatus regardless of the orientation of the apparatus. Such means include at least two sealing means G and G', respectively.

Tubular member 150 includes first stopping means 167 on its internal surface 151. First stopping means 167 is an annular ledge. First closure means 155 includes plug 170 adapted to firmly contact first stopping means 167 when first closure means 155 is firmly attached to tubular member 150. As shown, plug 170 is hollow and has open 172 and closed 173 ends and downwardly depending skirt 176 with internal 184 and external 185 surfaces. Skirt 176 is adapted to fit into first open end 153 of tubular member 150. Closed end 173 of first closure means 155 is formed by a bottom wall with internal 174 and external 175 surfaces. Closure means 155 also includes downwardly depending second annular skirt 178 with internal 179 and external 180 surfaces. Plug 170, as illustrated, is adapted so that beveled surface 177 of plug 170 contacts first stopping means 167 to form sealing means G. Second sealing means G' for forming a liquid tight seal between tubular member 150 and first closure means 155 includes at least one annular ring 157 on internal surface 179 of second annular skirt 178 in conjunction with external surface 152 of tubular member 150. As illustrated in FIGS. 8 and 9, optional sealing means G'' is formed at the junction of internal surface 151 of tubular member 150 and external surface 185 of plug 170 between first sealing means G and second sealing means G'.

Prior to assembling the apparatus of the present invention for use, fluid is poured into the apparatus such that the top of the fluid level is slightly above first stopping means 167. Thereafter, plug 170 is inserted into first open end 153 of tubular member 150. Beveled surface 177 of plug 170 firmly contacts first stopping means 167 to form sealing means G. External surface 185 of plug 170 also contacts internal surface 151 of tubular member 150 to form optional sealing means G''. The fluid which was originally above first stopping means 167 is forced into space 187 bound by sealing means G, lower portion 188 of external surface 185 of plug 170, portion 189 of internal surface 151 of tubular member 150 and optional sealing means G''.

A PROCEDURE FOR ISOLATION AND IDENTIFICATION OF A MICROORGANISM

The apparatus of the present invention is sterilized, e.g. using an autoclave, gamma irradiation or ethylene oxide. If a non-integral support is used, it should be inserted into the second closure means prior to sterilization. After sterilization the support is seeded with a suspension of cells susceptible to the microorganism of interest in a growth supporting cell culture medium. The cells are grown to confluency, for example 48-72 hours at 35°-39° C.

The second closure means and tubular member are filled with cell culture medium to a point slightly above the first stopping means. The first closure means is firmly attached to the tubular member so that the bottom or beveled surface of the first closure means contacts the first stopping means. Any excess liquid medium is thus forced into the upper portion of the tubular member and trapped.

Bottom walls of the first and the second closure means may be parallel to each other and composed of material permitting light transmission and the tubular member designed as a straight channel to provide an unobstructed optical path. Thus, the cell monolayer can be observed using a light microscope by placing the apparatus on an inverted light microscope with the apparatus in a vertical direction. Because inversion of the apparatus will not damage the cell monolayer, the apparatus can also be observed with a standard orientation light microscope by inverting the apparatus.

The cell culture medium is removed, for example by aspiration. Inoculum is added (at least about 0.2 ml of fluid containing the microorganism) to the apparatus. The first closure means is placed on the tubular member and the apparatus may be centrifuged, if required by the protocol. The apparatus may be removed from the centrifuge by grasping the septum with an instrument, such as with forceps.

After centrifugation, the first closure means is removed and the inoculum is withdrawn, if required by the assay protocol. The cell monolayer is refed by placing about 1.0 ml of "cell culture maintenance medium" into the apparatus. The first closure means is replaced and the apparatus is placed in an incubator for at least about 16-24 hours at about 36°-38° C. for growth of the microorganism.

Thereafter, the cell culture maintenance medium is removed by aspiration, and the cell monolayer is fixed by placing fixative (e.g. 1.0 ml of acetone) in the apparatus and letting stand (e.g. 10 minutes at room temperature). After fixation, the fixative is removed by aspiration.

Prior to staining, the fixed cell monolayer is dried preferably in air. The second closure means may be detached from the tubular member means to accelerate drying. Alternatively, the cell monolayer is rinsed briefly with phosphate buffered saline (PBS), or similar fluid, and the PBS aspirated prior to staining.

The cell monolayer is stained by adding 40-100 μl of reagent to the second closure means. Even coverage of the monolayer with reagent is achieved by gently tapping the second closure means. After the reagent is applied, the second closure means is placed in a moisture chamber (e.g. a petri dish with water saturated paper towels). Staining is allowed to proceed with the temperature and time conditions prescribed in the assay protocol being followed (e.g. 30 minutes at 35°-39° C.).

After staining, the reagent is removed by aspiration, and the remaining material is washed, for example with phosphate buffered saline (PBS) or with deionized or distilled water. Approximately 1.0 ml of fluid is pipetted into the apparatus, and swirled gently. The washing fluid is removed by aspiration and the remaining material is dried preferably in air.

Thereafter, if an insertable support is being used it is removed from the second closure means and mounted with appropriate mounting medium. The support is mounted by inverting the second closure means and placing it on a surface, for example on a microscope slide over a drop of mounting medium. If necessary, the support is released by tapping or distending the external wall of the bottom of the second closure means.

The mounted support can be observed as appropriate for the assay protocol being followed, for example, with a fluorescence or light microscope. Cytopathic effect or immunoperoxidase stained supports can be observed without removing the support from the second closure means.

Alternatively, if the second closure means is transparent or if the biological material is adhered to one or more surfaces of the apparatus, the biological material on the support or in the apparatus is observed as is appropriate to the protocol without removal of the sample.

Alternatively, other immunological or chemical analysis, e.g. enzyme immunoassays, can be performed in the apparatus of the present invention. Instruments such as spectrophotometers can be employed as is appropriate to the material being assayed and to the protocol.

Although the foregoing invention has been described in some detail by way of illustration and example for purposes of clarity of understanding, it will be obvious that certain changes and modifications may be practiced within the scope of the appended claims.

What is claimed is:

1. An apparatus for maintaining a biological sample on a support comprising
   a hollow tubular member with internal and external surfaces open at first and second opposed ends having first stopping means on said internal surface proximate said first end and
   first and second closure means adapted for sealing attachment to said tubular member at said first and said second ends, respectively, wherein said tubular member includes second stopping means on said external surface and said second closure means is open at a first end and closed by a bottom wall having internal and external surfaces at a second opposed end and a side wall having internal and external surfaces, the distance between said second open end of said tubular member and said internal surface of said bottom wall when said tubular member is firmly attached to said second closure means being less than the diameter of the support and the internal diameter of said tubular member at said second end is less than the diameter of the support.

2. The apparatus of claim 1 wherein said second closure means is open at a first end and closed by a bottom wall having internal and external surfaces at a second opposed end and a side wall having internal and external surfaces said internal surface of said side wall being narrowed the distance between said second open end of said tubular member and said internal surface of said bottom wall when said tubular member is firmly attached to said second closure means being less than the diameter of the support and the internal diameter of said tubular member at said second end is less than the diameter of the support.

3. The apparatus of claim 1 wherein said first closure means comprises a plug adapted to firmly contact said first stopping means when said first closure means is firmly attached to said tubular member.

4. The apparatus of claim 3 wherein said plug comprises a hollow cylinder having an open end and a closed end formed by a bottom wall having internal and external surfaces and downwardly depending skirt adapted to fit into said first open end of said tubular member.

5. The apparatus of claim 4 wherein said plug includes a beveled surface.

6. The apparatus of claim 4 wherein said plug further comprises a second annular skirt having internal and external surfaces and attached to and depending from a top portion of said plug and having a diameter greater than the external diameter of said first end of said tubular member.

7. The apparatus of claim 6 wherein said apparatus includes sealing means between said tubular member and said second annular skirt.

8. The apparatus of claim 7 wherein said sealing means comprises at least one annular ring on said internal surface of second annular skirt proximate said top portion of said plug in conjunction with said external surface of said tubular member.

9. The apparatus of claim 7 wherein said sealing means comprises at least one annular ring on said external surface of said tubular member proximate said first end of said tubular member in conjunction with said internal surface of said second annular skirt.

10. The apparatus of claim 6 wherein said plug includes gripping means.

11. The apparatus of claim 10 wherein said gripping means comprises at least one ridge on said external surface of said second annular skirt.

12. The apparatus of claim 10 wherein said gripping means includes a septum attached to opposed sides of said hollow cylinder.

13. The apparatus of claim 6 wherein said second annular skirt is longer than said first annular skirt.

14. The apparatus of claim 1 wherein said second closure means comprises a hollow cylinder and the junction of said internal surface of said side wall and said internal surface of said bottom wall is beveled.

15. The apparatus of claim 1 wherein said second stopping means comprises at least two discontinuous projections.

16. The apparatus of claim 1 wherein said second stopping means comprises an annular shoulder.

17. The apparatus of claim 1 wherein said tubular member includes proximate said second end means for grasping said apparatus.

18. The apparatus of claim 17 wherein said grasping means comprises a raised textured surface.

19. The apparatus of claim 1 wherein said apparatus includes means for maintaining a support in contact with medium regardless of the orientation of said apparatus.

20. The apparatus of claim 1 including means for maintaining said support in contact with a liquid medium comprising at least two sealing means between said tubular member and said first closure means.

21. The apparatus of claim 20 wherein said second sealing means comprises said internal surfaces of said tubular member in conjunction with said external surface of said first closure means.

22. The apparatus of claim 20 wherein said second sealing means comprises an annular ring on said internal surface of said tubular member in conjunction with an external surface of said first closure means.

23. The apparatus of claim 20 wherein said second sealing means comprises said internal surface of said tubular member in conjunction with an annular ring on an external surface of said first closure means.

24. The apparatus of claim 20 wherein said first sealing means comprises said first stopping means in conjunction with a surface of said first closure means.

25. The apparatus of claim 24 wherein said stopping means comprises an annular ledge and said surface of first closure means comprises an external surface of a bottom wall of said first closure means.

26. The apparatus of claim 24 wherein said first stopping means is beveled and said surface of said first closure means is beveled.

27. The apparatus of claim 1 wherein said apparatus includes a sealing means for forming a liquid tight seal between said tubular member and said second closure means.

28. The apparatus of claim 27 wherein said sealing means comprises at least one annular ring on an internal surface of a side wall of said second closure means.

29. The apparatus of claim 27 wherein said sealing means comprises at least one annular ring on said external surface of said tubular member proximate said second end.

30. The apparatus of claim 1 wherein said second closure means includes means for releasing a support therefrom.

31. The apparatus of claim 30 wherein said means for releasing a support releases said support from said internal surface of said bottom wall.

32. The apparatus of claim 31 wherein said releasing means comprises at least one groove on said internal surface of said bottom wall.

33. The apparatus of claim 31 wherein said releasing means comprises at least one ridge on said internal surface of said bottom wall.

34. The apparatus of claim 31 wherein said releasing means comprises at least one longitudinal groove on said internal surface of said side wall.

35. The apparatus of claim 31 wherein said bottom wall of said second closure means is flexible.

36. The apparatus of claim 1 wherein said support is a glass disk.

37. The apparatus of claim 1 wherein said biological sample is an adherent cell culture.

38. The apparatus of claim 1 adapted for isolating and culturing microorganisms.

39. The apparatus of claim 1 wherein said apparatus includes means for detection of said biological sample without removal of said support from said second closure means.

40. The apparatus of claim 39 wherein said means includes said second closure means having a translucent bottom wall.

41. An apparatus for maintaining a biological sample on a support comprising
a hollow cylindrical tube with internal and external surfaces and first and second opposed open ends, said tube having first stopping means on said internal surface proximate said first end and second stopping means on said external surface proximate said second end and first and second closure means adapted for attachment to said tube at said first and second ends, respectively;
said first closure means comprising (1) a top portion, (2) a first annular skirt depending from the underside of said top portion and adapted to be inserted into said first end of said tube and having a closed end formed by a bottom wall generally parallel to said top portion, said bottom wall of said closure means contacting said first stopping means when said first closure means is firmly attached to said tube and (3) a second annular skirt attached to and depending from the periphery of said top portion of said first closure means having a diameter greater than the external diameter of said first end of said tube; and
said second closure means comprising a generally cylindrical structure open at one end and closed by a bottom wall having internal and external surfaces at a second opposed end and a side wall having internal and external surfaces, the distance between said second open end of said tube and said internal surface of said bottom wall when said tube and said second closure means are seated together being less than the diameter of the support and the internal diameter of said tube at said second end being less than the diameter of the support such that when the apparatus is assembled said apparatus includes means for maintaining said sample in contact with a solid column of fluid, regardless of the orientation of said apparatus and means for maintaining the original orientation of said support.'

42. The apparatus of claim 41 wherein said first stopping means comprises an annular ledge.

43. The apparatus of claim 41 wherein said second stopping means comprises at least two discontinuous projections.

44. The apparatus of claim 41 wherein means for maintaining said support in contact with said column of fluid comprise two sealing means between said tube and said first closure means.

45. The apparatus of claim 44 wherein said first sealing means includes said first stopping means in conjunction with an external surface of said first annular skirt.

46. The apparatus of claim 44 wherein said second sealing means includes an internal surface of said tube in conjunction with said external surface of said first annular skirt.

47. The apparatus of claim 41 wherein said second closure means has at least one annular ring on said external surface of tubular member.

48. The apparatus of claim 41 wherein said tube includes proximate said second end means for grasping said apparatus.

49. The apparatus of claim 41 wherein said second annular skirt is longer than said first annular skirt.

50. The apparatus of claim 41 wherein said second closure means includes means for releasing a support from said internal surface of said bottom wall.

51. The apparatus of claim 50 wherein said releasing means comprises at least one groove on said internal surface.

52. The apparatus of claim 50 wherein said releasing means comprises at least one longitudinal groove on said internal surface of said side wall of said first closure means.

53. An apparatus for transporting a biological sample on a support comprising a hollow cylindrical tube with internal and external surfaces at first and second opposed open ends, said tube having a stopping means on said internal surface proximate said first end and first and second closure means adapted for attachment to said tube at said first and second ends, respectively;

said first closure means comprising (1) a top portion, (2) a first annular skirt depending from the underside of said top portion and adapted to be inserted into said first end of said tube and having a closed end formed by a bottom wall generally parallel to said top portion, said bottom wall of said closure means contacting said first stopping means when said first closure means is firmly attached to said tube and (3) a second annular skirt attached to and depending from the periphery of said top portion of said first closure means having a diameter greater than the external diameter of said first end of said tube; and said second closure means comprising a generally cylindrical structure open at one end and closed by a bottom wall at a second opposed end and a side wall having internal and external surfaces and said internal surface of said side wall is narrowed, the distance between said second open end and said external surface of said bottom wall of said closure means when said tube is firmly attached to said second closure means being less than the diameter of the support and the internal diameter of said tube at said second open end being less than the diameter of the support; such that when the apparatus is assembled said apparatus includes means for maintaining said sample in contact with a solid column of fluid, regardless of the orientation of said apparatus and means for maintaining the original orientation of said support.

54. The apparatus of claim 53 wherein said stopping means comprises an annular ledge.

55. The apparatus of claim 54 wherein means for maintaining said support in contact with said column of fluid comprises two sealing means for forming a liquid tight seal between said tube and said first closure means wherein said first sealing means includes at least one annular ring on said internal surface between said tube and said first closure means.

56. The apparatus of claim 55 wherein said first sealing means includes said first stopping means in conjunction with an internal surface of said first annular skirt.

57. The apparatus of claim 55 wherein said second sealing means includes an internal surface of said tube in conjunction with said external surface of said first annular skirt.

58. The apparatus of claim 54 wherein said annular ledge is beveled and said second closure means includes a beveled surface.

59. The apparatus of claim 53 wherein said tube includes at least one annular ring on said exterior surface proximate said second open end.

60. The apparatus of claim 53 wherein said second closure means has at least one annular ring on said internal surface of said side wall.

61. The apparatus of claim 53 wherein said tube includes means for grasping said apparatus proximate said second end.

62. The apparatus of claim 53 wherein said second annular skirt is longer than said first annular skirt.

63. The apparatus of claim 53 wherein said second closure means includes a means for releasing a support from said internal surface of said bottom wall.

64. The apparatus of claim 63 wherein said releasing means comprises at least one groove on said internal surface.

* * * * *